(12) United States Patent
Nabat et al.

(10) Patent No.: US 9,517,356 B2
(45) Date of Patent: Dec. 13, 2016

(54) OPTICAL THERAPEUTIC APPARATUS

(71) Applicants: Craig Nabat, Tustin, CA (US);
Chung-Yang Mike Chen, Irvine, CA (US)

(72) Inventors: Craig Nabat, Tustin, CA (US);
Chung-Yang Mike Chen, Irvine, CA (US)

( * ) Notice: Subject to any disclaimer, the term of this patent is extended or adjusted under 35 U.S.C. 154(b) by 288 days.

(21) Appl. No.: 13/622,800

(22) Filed: Sep. 19, 2012

(65) Prior Publication Data

US 2013/0331640 A1    Dec. 12, 2013

(51) Int. Cl.
*A61N 5/06* (2006.01)
*A61M 21/02* (2006.01)
*A61M 21/00* (2006.01)

(52) U.S. Cl.
CPC ............ *A61N 5/0619* (2013.01); *A61M 21/02* (2013.01); *A61M 2021/0027* (2013.01); *A61N 2005/0605* (2013.01); *A61N 2005/0647* (2013.01); *A61N 2005/0652* (2013.01); *A61N 2005/0659* (2013.01); *A61N 2005/0662* (2013.01)

(58) Field of Classification Search
CPC ..................... A61N 5/0619; A61N 2005/0647; A61N 2005/0642; A61N 2005/0643; A61N 2005/0645; A61M 21/00; A61M 21/02; A61M 2021/0005; A61M 2021/0027; A61M 2021/0044
USPC .................................. 600/26–28; 607/88–91
See application file for complete search history.

(56) References Cited

U.S. PATENT DOCUMENTS

| | | | |
|---|---|---|---|
| 6,013,096 A | 1/2000 | Tucek | |
| 6,074,411 A | 6/2000 | Lai et al. | |
| 6,702,767 B1 * | 3/2004 | Douglas et al. | ............... 601/15 |
| 7,993,381 B2 | 8/2011 | Mac et al. | |
| 8,043,348 B2 | 10/2011 | Weber | |
| 2004/0044384 A1 * | 3/2004 | Leber et al. | ................ 607/88 |
| 2008/0046042 A1 * | 2/2008 | Branch | ................ 607/88 |
| 2009/0088822 A1 * | 4/2009 | Pruitt et al. | ................ 607/89 |

* cited by examiner

*Primary Examiner* — Charles A Marmor, II
*Assistant Examiner* — Carrie R Dorna
(74) *Attorney, Agent, or Firm* — Rosenberg, Klein & Lee (57) ABSTRACT

An optical therapeutic apparatus includes an ear shield for covering a wearer's ear, which has a plurality of acupuncture points; a hanging member including a connection portion connected to the ear shield; and a plurality of light emitters disposed within an interior portion of the ear shield in array manner to face the plurality of acupuncture points respectively. The plurality of light emitters includes a plurality of acupoint-stimulation elements, each corresponding to a respective one of the acupuncture points, at least two sets of the acupoint-stimulation elements are capable of emitting stimulation light beams at different time intervals.

19 Claims, 7 Drawing Sheets

OPTICAL THERAPEUTIC APPARATUS

BACKGROUND OF THE INVENTION

1. Field of the Invention

The present invention relates to an optical therapeutic apparatus, more particularly to an optical therapeutic apparatus that is adapted to be worn overhead or around a wearer's ear.

2. Description of the Background Art

A majority of people of today have long working hours and hence stress follows due to lack of leisure time for taking physical exercise. The environment we are living in is often full of disturbing noises so as to cause our nervous system tension, thus leading to constant stress and fatigue. In addition, due to long time working and sitting in front of a computer, one is susceptible to be muscle-bound, that is, to experience much generalized muscular tension. Under such an awful repetition of a stressful environment, our bodily-function ability will easily deteriorate.

However, when we suffer from headache, back pain, etc. due to tension of the nervous system or mental stress, we might visit a doctor, who reminds us not to rely on pain-killing pills for a long period. Rather, he suggests for us to do some massage method in order to relax our body's muscles and mind. Massage treatment can not only relax our muscles, but some forms of massage treatment also stimulate the acupuncture points of the human body. Such stimulation subsequently corrects our nervous centre, and hence stimulates all the endocrine glands in such a manner that the physical function of our body returns to its normal condition.

Some of the well-known common massage treatments, including foot massage, neck-and-shoulder massage, and abdomen massage, are intended for particular parts of the human body. Ear massage also is very common to all people. Because the ear is mainly made up of cartilage, if massaged improperly by force, the force can often lead to blood stasis in the ears and may cause injury to the cartilage and hence deformation of the ears. Improper treatment to the ears cannot bring a healthy advantage, but may cause harm to the ears, and such treatment would not be welcome.

In order to prevent the ear from being massaged improperly by force, low-energy laser, or light beam projection, can be applied to replace the traditional ear massage to stimulate the acupuncture points of the ear. For example, in article of "The Use of Laser on Acupuncture Points for Smoking Cessation" published in *American Journal of Acupuncture Vol.* 15(2), C. H. Tan, et al., discloses that it is effective for human beings to achieve smoking cessation through the means of projecting laser toward the acupuncture points (acupoints) of the ear to stimulate the acupuncture points of Shenmen, Yuanzhong and Fei. More preferably, when stimulating the acupuncture points of Shenmen, Yuanzhong and Fei, it is better to synchronously stimulate the acupuncture points of Neifenmei and Shenshangxian to obtain better efficiency of smoking cessation.

Moreover, along with the development of laser technology, the traditional acupuncture and moxibustion technology (use of mugwort herb) is being gradually replaced by the laser technology. Through utilizing the special optical properties of laser, energy can be concentrated on the acupuncture points to generate a more curative effect.

However, up to now, the method for stimulating acupuncture points via low-energy laser or light beam projection in the prior art, such as disclosed by U.S. Pat. No. 7,993,381, U.S. Pat. No. 6,013,096, and U.S. Pat. No. 6,074,411, still requires manual holding of the laser projecting device to make the laser project toward the acupuncture points exactly, so that it is not only inconvenient for operation, but also may cause the projection position of the laser beam become unstable. Thus, the method in the prior art would cause the reduction of curative effect.

SUMMARY OF THE INVENTION

Therefore, an object of the present invention is to provide an optical therapeutic apparatus, more particularly to an optical therapeutic apparatus that is adapted to be worn overhead or around a wearer's ear, and that can provide optical stimulation massage to the wearer's ear, thereby preventing damage or injury caused by improper massage pressure of the conventional massage treatment, and making the laser beam exactly project toward the acupuncture points free from manually holding the laser projecting device by hands.

The optical therapeutic apparatus of the present invention is adapted to be worn overhead or around a wearer's ear, and includes an ear shield for covering a wearer's ear, which is formed with a plurality of acupuncture points; a rear shield disposed behind the ear shield to include a connection portion connected to the ear shield; and a plurality of light emitters disposed within an interior portion of the ear shield in array manner to face the plurality of acupuncture points respectively. The plurality of light emitters includes a plurality of acupoint-stimulation elements, each corresponding to a respective one of the acupuncture points, at least two sets of the acupoint-stimulation elements are capable of emitting stimulation light beams at different time intervals.

Preferably, said acupoint-stimulation elements correspond to at least one of the acupuncture points of Shenmen, Yuanzhong and Fei.

In one preferred embodiment, the wavelength of the stimulation light beam ranges from about 450 nm to about 1000 nm. Two sets of the acupoint-stimulation elements are capable of emitting stimulation light beams at different time intervals.

In another embodiment, the plurality of light emitters further includes a plurality of auxiliary-stimulation elements capable of emitting a plurality of auxiliary stimulation light beams ranging from about 450 nm to about 1000 nm. In addition, the auxiliary stimulation light beam and the stimulation light beam may have wavelength different from each other.

Preferably, the plurality of light emitters consists of LEDs (Light Emitting Diodes) or laser modules.

In one preferred embodiment, the ear shield is provided with a circular soft cushion at an exterior thereof for tightly abutting against the wearer's ear. The ear shield is further provided with a positioning lid within the interior portion, inward to the circular soft cushion and is formed with a plurality of fixing holes for respectively holding the plurality of light emitters therein.

Preferably, the rear shield is in the form of an adjustable curve structure, and includes a display screen for displaying a radiating time and a regulator knob operable to alter the radiating time. The ear shield is provided with a loud speaker for broadcasting a sound, which could be a voice message. The rear shield further can be provided a transmission cable for capturing a frequency signal from a voice producing device and transferring the frequency signal to the loud speaker for broadcasting of the voice message. The transmission cable can be adapted to be coupled electrically to a power source in order to obtain an electrical power for illuminating the plurality of light emitters. The optical therapeutic apparatus further includes an activation switch coupled electrically to the plurality of light emitters for switching-on and switching-off of the plurality of light emitters.

The rear shield is also provided with a buzzer or alarm, which is capable of generating a reminding alarm at a pre-set time interval.

When compared to the prior art optical therapeutic apparatus, due to utilization an ear shield in the optical therapeutic apparatus of the present invention for covering a wearer's ear and a plurality of light emitters consisting of a first acupoint-stimulation element, a second acupoint-stimulation element and a third acupoint-stimulation element in order to stimulate the plurality of acupuncture points of the wearer's ear, massage effects are imparted to the acupuncture points of the wearer's ear, while preventing injury caused thereto, and further preventing unstable operation caused by manually holding the laser projecting device. In addition, due to different time intervals for emitting the stimulation light beams, the different acupuncture points of the wearer's ear are respectively and optionally stimulated.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE EMBODIMENTS

The present invention relates to an optical therapeutic apparatus, more particularly to an optical therapeutic apparatus that is adapted to be worn overhead or around a wearer's ear. A preferred embodiment is illustrated in the following paragraphs for better understanding of the present invention, however the scope of the invention should not be limited only thereto.

Figure 1:
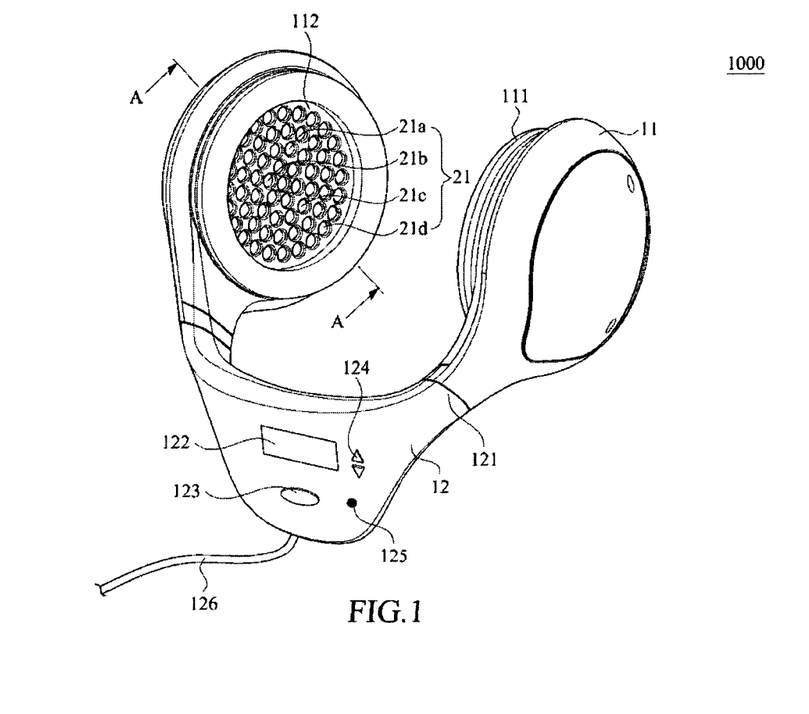
FIG. 1 shows a perspective view of an optical therapeutic apparatus of the present invention that is adapted to be worn overhead or around a wearer's ear.
Figure 2:
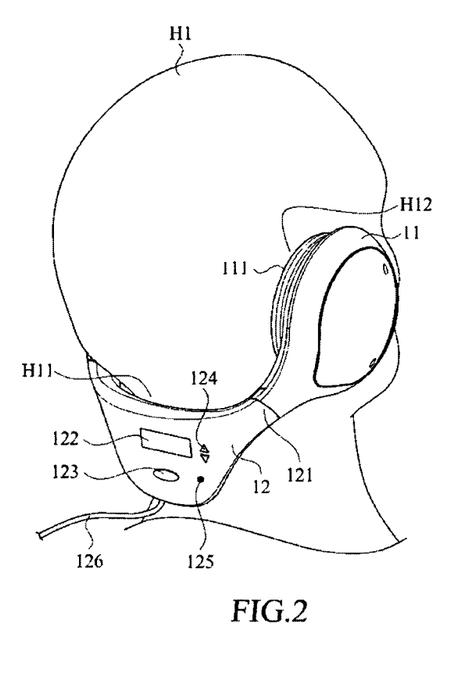
FIG. 2 illustrates the optical therapeutic apparatus of the present invention in application.
Figure 3:
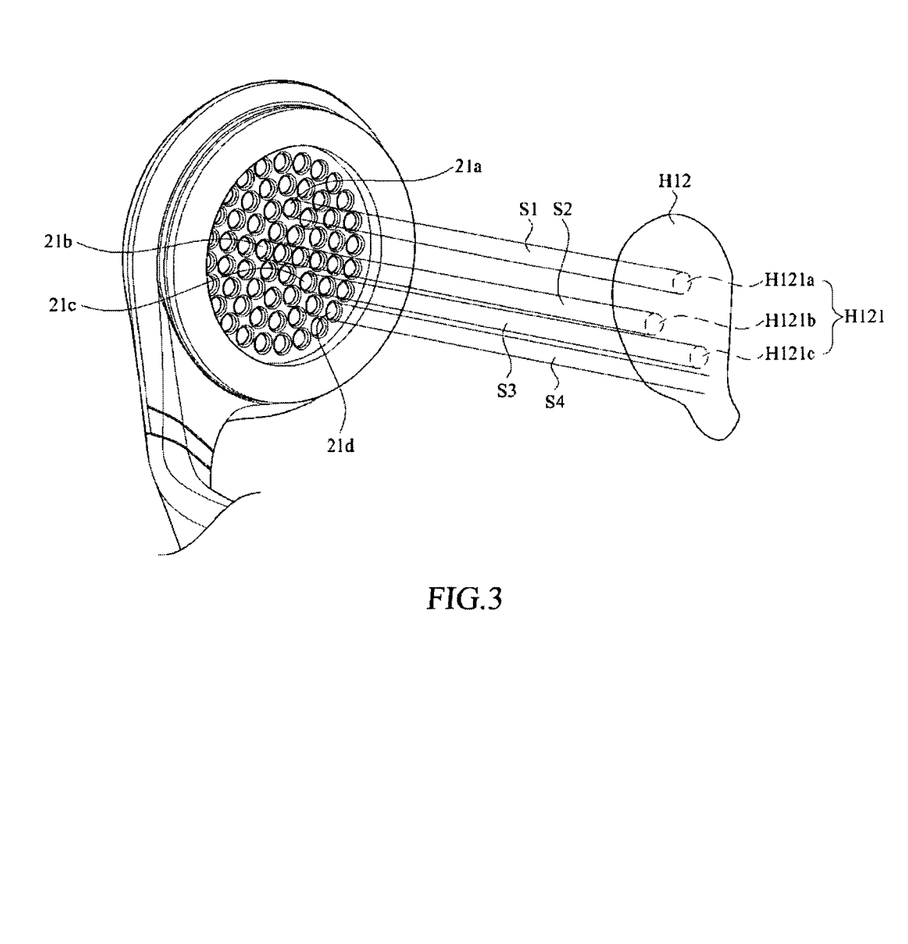
FIG. 3 shows how an ear shield of the optical therapeutic apparatus of the present invention stimulates the acupuncture points in a wearer's ear.

Refer to FIGS. 1 to 3, wherein FIG. 1 shows a perspective view of an optical therapeutic apparatus of the present invention that is adapted to be worn overhead or around a wearer's ear; FIG. 2 illustrates the optical therapeutic apparatus of the present invention in application; while FIG. 3 shows how an ear shield of the optical therapeutic apparatus of the present invention stimulates the acupuncture points in a wearer's ear. As illustrated, the optical therapeutic apparatus 1000 of the present invention is adapted to be worn overhead or around a wearer's ear 1112 (see FIG. 2), which is formed with a plurality of acupuncture points H121. The optical therapeutic apparatus 1000 of the present invention accordingly includes an ear shield 11, a hanging member 12, and a plurality of light emitters 21.

The ear shield 11 is used for covering the wearer's ear H12. The ear shield 11 is provided with a circular soft cushion 111 at an exterior portion thereof for tightly abutting against the wearer's ear. The hanging member 12 can be disposed behind the ear shield 11 to abut against the rear side of the wearer's neck H11 in order to maintain stability of the optical therapeutic apparatus 1000 of the present invention when in application. The hanging member 12 includes a connection portion 121 connected to the ear shield 11. Moreover, the hanging member 12 also can be configured to hang on the wearer's head H1.

The plurality of light emitters 21 are disposed within the interior portion of the ear shield 11 in array manner in order to face the plurality of acupuncture points H121 of the wearer's ear respectively. The plurality of light emitters 21 preferably includes a first acupoint-stimulation element 21a, a second acupoint-stimulation element 21b, a third acupoint-stimulation element 21c and a plurality of auxiliary-stimulation elements 21d (only one is shown in FIG. 1).

Figure 4:
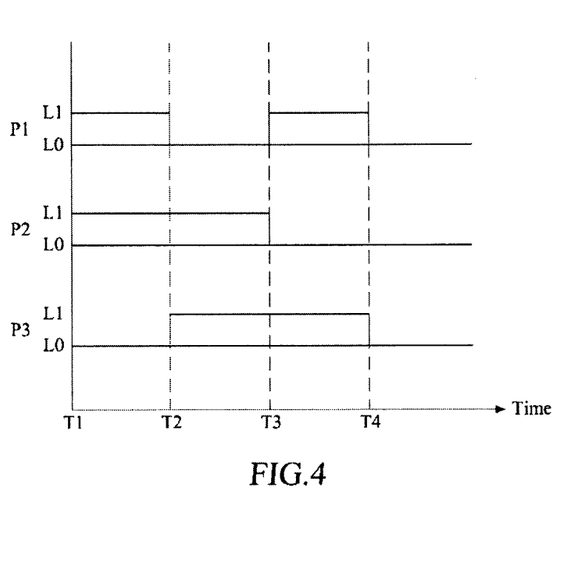
FIG. 4 shows a diagram of time intervals relative wave lengths of the stimulation light beams resulted from utilization of the optical therapeutic apparatus of the present invention.

Refer to FIG. 3 and FIG. 4, wherein FIG. 4 shows a diagram of time intervals relative wave lengths of the stimulation light beams resulted from utilization of the optical therapeutic apparatus 1000 of the present invention. As shown, the first acupoint-stimulation element 21a emits a first stimulation light beam S1 in accordance with a first time interval P1 in order to stimulate the first acupuncture point H121a in the wearer's ear H12 (see FIG. 3). The second acupoint-stimulation element 21b emits a second stimulation light beam S2 in accordance with a second time interval P2 in order to stimulate the second acupuncture point H121b in the wearer's ear H12. The third acupoint-stimulation element 21c emits a third stimulation light beam S3 in accordance with a third time interval P2 in order to stimulate the third acupuncture point H121c in the wearer's ear H12. Preferably, the first acupuncture point H121a can be the acupuncture point of Shenmen, the second acupuncture point H121b can be the acupuncture point of Fei, and the third acupuncture point H121c can be the acupuncture point of Yuanzhong. However, other acupoints may be used as understood by an ordinary practitioner of the acupuncture arts.

Additionally, it shall be noted that the first acupoint-stimulation element 21a is in the light emitting mode L1 from the first timing T1 to the second timing T2, in the suspending mode L0 from the second timing T2 to the third timing T3 and again in the light emitting mode L1 from the third timing T3 to the fourth timing T4. Since the first timing T1 overlaps with the fourth timing T4, a first time interval is thus formed. Because the second and third time intervals P2, P3 of the second and third acupoint-stimulation elements 21b, 21c are the same as the first acupoint-stimulation elements 21a, those skilled in the art can observe from the diagram shown in FIG. 4 that the time interval to emit light waves of different wavelengths so as to optionally stimulate the acupuncture points H121 in the wearer's ear H12 can be set in accordance with the user's requirement. Meanwhile, the auxiliary-stimulation elements 21d (only one is shown in FIG. 1) are capable of emitting constantly a plurality of auxiliary stimulation light beams S4 in order to stimulate other points of the wearer's ear H12 offset to the acupuncture points H121 respectively until the optical therapeutic apparatus 1000 of the present invention is switched off. Therapeutic auxiliary acupuncture points also are well-known to those skilled in the acupuncture arts.

In one preferred embodiment, each of the first stimulation light beam S1, the second stimulation light beam S2, the third stimulation light beam S3 and the auxiliary stimulation light beam 4 has a wavelength ranging from about 450 nm to about 1000 nm with the stimulation light beams S1,S2, S3, S4 being emitted at different time intervals. Preferably, the first acupoint-stimulation element 21a is an LED (Light Emitting Diode), which emits the first stimulation light beam S1 at about 880 nm wavelength. The second acupoint-stimulation element 21b is also an LED (Light Emitting Diode), which emits the second stimulation light beam S2 ranging from about 600 nm to about 1000 nm wavelength. The third acupoint-stimulation element 21c is a laser module, which emits the first stimulation light beam S1 at about 640 nm wavelength. The auxiliary-stimulation element 21d also is an LED, which emits the auxiliary stimulation light beam S4 at about 450 nm wavelength.

The above-mentioned wavelengths and the light emitting elements 21 are some examples only, any other light sources capable of providing different wavelengths and massage effects to the wearer's ear H12 can be a substitute in the present invention.

Figure 5:
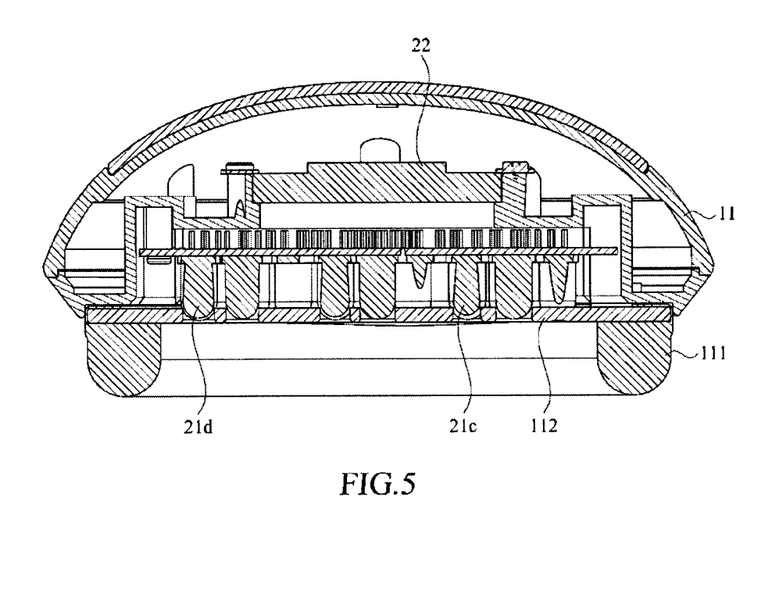
FIG. 5 is a cross-sectional view of the optical therapeutic apparatus of the present invention taken along the line A-A in FIG. 1.

Refer to FIGS. 1 and 5, wherein FIG. 5 is a cross-sectional view of the optical therapeutic apparatus of the present invention, taken along the line A-A in FIG. 1. As illustrated, the ear shield 11 is further provided with a positioning lid 112 within the interior portion, inward of the circular soft cushion 111, and is formed with a plurality of fixing holes (not shown) for respectively holding the plurality of light emitters 21 therein. The ear shield 11 is also provided a loud speaker 22 for broadcasting a voice message.

In this embodiment, the hanging member 12 is provided a transmission cable 126 for capturing a frequency signal from a voice producing device (for example, a compact disc or MP3 player, not shown) and transferring the frequency signal to the loud speaker 22 for broadcasting as the voice message. The frequency signal also may be music or therapeutic sounds. The transmission cable 126 can be adapted to be coupled electrically to a power source in order to obtain an electrical power for illuminating the plurality of light emitters 21. Preferably, the hanging member 12 is in the form of an adjustable curve structure for ergonomically conforming to the wearer' head or ear.

The hanging member 12 further has a display screen 122 and a regulator knob 124. The display screen 122 is provided for displaying a radiating time and a function selection interface (not shown). The regulator knob 124 that is operable to alter the radiating time of a respective light emitting element 21 and to operate said function selection interface. The hanging member 12 is further provided with an activation switch 123 that can be coupled electrically to the plurality of light emitters 21 for switching-on and switching-off of the plurality of light emitters 21. The hanging member 12 is also provided with a buzzer 125 or alarm, which is capable of generating a reminding alarm at a pre-set time interval.

Figure 6:
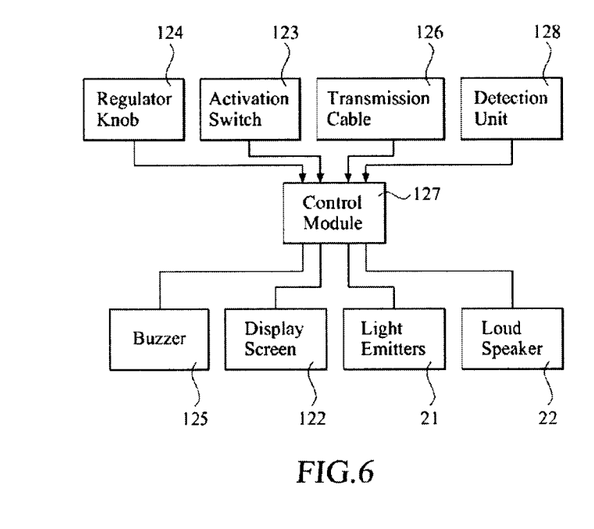
FIG. 6 is a block diagram illustrating the function system in the optical therapeutic apparatus of the present invention.

FIG. 6 is a block diagram illustrating the function system in the optical therapeutic apparatus 1000 of the present invention. The optical therapeutic apparatus 1000 of the present invention further includes a control module 127, which is electrically coupled to the display 122, the activation switch 123, the regulator knob 124, the buzzer 125, the transmission cable 126, the light emitting elements 21 and the loud speaker 22. The user can manipulate the regulator knob 124 in such a manner to alter the radiating time of a respective light emitting element 21 so that the activation switch 123 transmits an ON/OFF signal to the respective light emitting element 21 for emitting the stimulation light beam toward the wearer's ear H12.

Moreover, once the radiating time is set, the radiating time is displayed over the display 122. The countdown time is arranged in such a manner that the control module 127 activates the buzzer 125 at a pre-set time interval to generate a reminding alarm, thereby informing and preventing injury caused to the user of the optical therapeutic apparatus of the present invention due to overuse.

Note that the transmission cable 126 is capable of capturing a frequency signal from the voice producing device and transferring the frequency signal to the loud speaker 22 for broadcasting as the voice message (i.e., music or songs), which enable the user of the optical therapeutic apparatus of the present invention to listen to the music, hence causing relaxation of mind. Additionally, the transmission cable 126 is adapted to be coupled electrically to a power source in order to obtain an electrical power for illuminating said plurality of light emitters.

The optical therapeutic apparatus 1000 of the present invention further includes a memory device (not visible) for storing sound data (i.e., voice, music, or both) and can be adapted to be coupled electrically to the control module 127. Under this condition, during the application of the optical therapeutic apparatus of the present invention, the control module 127 can retrieve sound data from the memory device so as to be played over the loud speaker 22 as voice message. In other words, the user of the optical therapeutic apparatus 1000 of the present invent can enjoy his or her favorite music or songs while being massaged, hence resulting in relaxation of muscles and mind.

The optical therapeutic apparatus according to present invention may include a detection unit 128 or sensor coupled electrically to the control module 127 for detecting absence of the apparatus from the wearer's ear. An infrared sensing device may serve the purpose of the detection unit 128 for detecting the infrared light wave reflected from the wearer's ear. Upon detecting there is no infrared light wave reflected from the wearer's ear, the detection unit 128 transmits a stop signal or countdown signal to the control module 127, which deactivates the illumination of the light emitting elements 21. Moreover, in the event of detecting presence of infrared light wave, the detection unit 128 may activate the control module 127 again to re-activate the light emitting elements 21, which, in turn, emit the stimulation light beams continuously until the countdown time.

Figure 7:
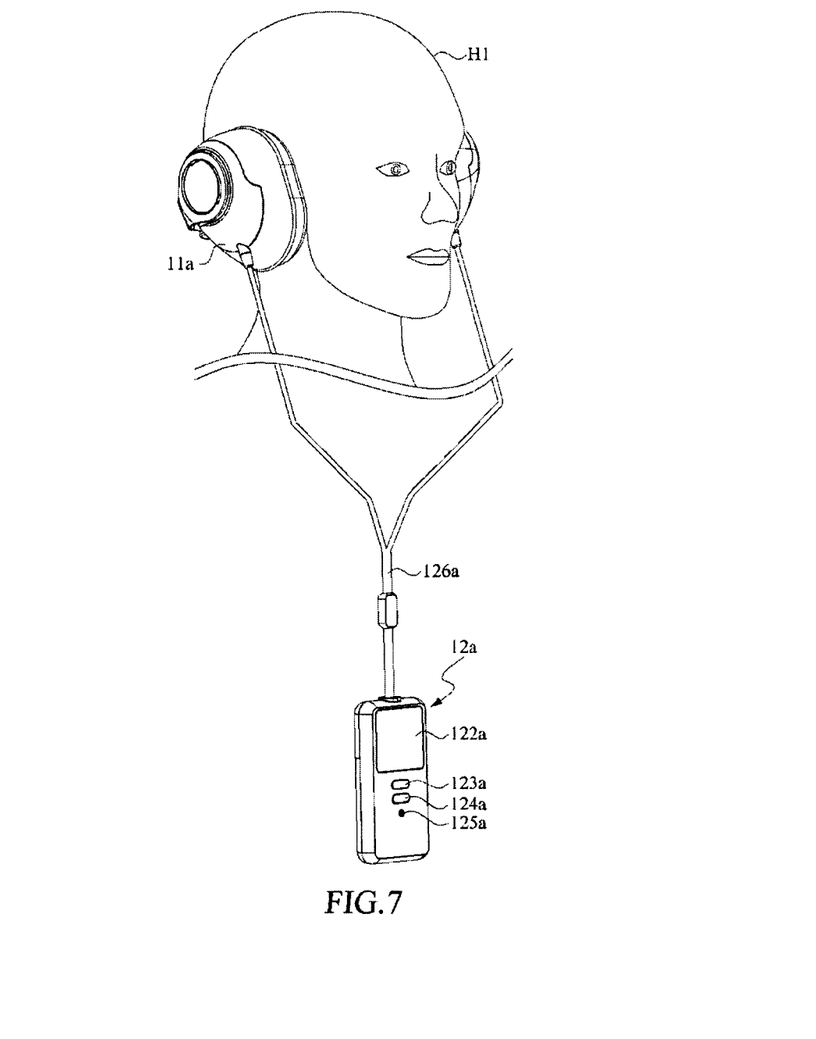
FIG. 7 is a perspective illustration of an embodiment, in accordance with the present invention.

Please refer to FIG. 7, which presents another embodiment of the present invention. With difference from the embodiment presented in FIG. 1, in this embodiment, a controller 12a is capable of electrically connecting to at least one ear shield 11a via a transmission cable 126a. The controller 12a is configured with a display screen 122a, an activation switch 123a, a regulator knob 124a and a buzzer 125a performing functions respectively similar to the display screen 122, the activation switch 123, the regulator knob 124 and the buzzer 125a. Therefore, it is unnecessary for the wearer to put his hand behind his neck to operate regulator knob 124a any more because he can directly operate the regulator knob 124a of the controller to alter the radiating time of a respective light emitting element 21 and to operate said function selection interface. Thus, through the utilization of this embodiment, it can bring more operable convenience for the user (wearer).

When compared to the prior art optical therapeutic apparatus, the present embodiments prevent injury caused to the ear, and further prevent unstable operation caused by manually holding the laser projecting device. These salutary effects are due to utilization of ear shield 11 for covering a wearer's ear H12 and a plurality of light emitters 21 consisting of a first acupoint-stimulation element 21a, a second acupoint-stimulation element 21b and a third acupoint-stimulation element 21c in order to stimulate the plurality of acupuncture points H121 of the wearer's ear H12, hence causing massage effects at the acupuncture points H121 of the wearer's ear 1412. In addition, due to different time intervals for emitting the stimulation light beams, the different acupuncture points H121 of the wearer's ear H12 are respectively and optionally stimulated.

Due to the provision of the loud speaker in the optical therapeutic apparatus of the present invention, the user can listen to the sound message (i.e., voice, music, or songs) while being massaged; hence the nervous system and the mind of the user will be relaxed simultaneously.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An optical therapeutic apparatus, comprising:
    a pair of ear shields for covering a wearer's ears, which ears are disposed with a respective plurality of auricular acupuncture points;
    a hanging member including a connection portion connected to each ear shield, and wherein the hanging member is fitted as a headset, the hanging member further including a display screen for displaying a radiating time and a function selection interface, and a regulator knob operable to alter the radiating time and to operate the function selection interface;
    an array of light emitters disposed in the ear shields in juxtaposed opposition to the plurality of auricular acupuncture points respectively, the array of light emitters including a plurality of acupoint-stimulation elements, each element corresponding to a respective one of the auricular acupuncture points, at least two acupoint-stimulation elements emitting at least two respective stimulation light beams at different respective time intervals;
    a pair of loud speakers disposed in the ear shields directed to emit therapeutic sound or music into ears of the wearer;
    a control module operably coupled to the regulator knob, the display screen, the pair of loudspeakers, and the array of light emitters; and
    a detection unit electrically coupled to the control module, the detection unit transmitting a signal to the control module to activate the array of light emitters when presence of the wearer's ear is detected and deactivate the array of light emitters when absence of the wearer's ear is detected;
    wherein at least one of the acupoint-stimulation elements emits a first stimulation light beam to the auricular acupuncture point of Shenmen,
    wherein at least one of the acupoint-stimulation elements emits a second stimulation light beam to another auricular acupuncture point,
    wherein the acupoint-stimulation elements emit an infrared stimulation light beam or a visible stimulation light beam,
    wherein the therapeutic sound or music, in conjunction with the stimulation light beams, induces a state of wakeful relaxation in the wearer.

2. The optical therapeutic apparatus according to claim 1, wherein the plurality of acupoint-stimulation elements emit stimulation light beams with varying frequencies.

3. The optical therapeutic apparatus according to claim 1, wherein a wavelength of each of said plurality of stimulation light beams ranges from about 450 nm to about 1000 nm.

4. The optical therapeutic apparatus according to claim 1, wherein the stimulation light beams emitted from the at least two acupoint-stimulation elements respectively have frequencies that are different from one another.

5. The optical therapeutic apparatus according to claim 1, wherein the array of light emitters further includes a plurality of auxiliary-stimulation elements facing toward the wearer's ear are capable of emitting a constant plurality of auxiliary stimulation light beams in order to stimulate other points of the wearer's ear juxtaposed to the acupuncture points respectively.

6. The optical therapeutic apparatus according to claim 5, wherein each of said plurality of auxiliary stimulation light beams ranges from about 450 nm to about 1000 nm.

7. The optical therapeutic apparatus according to claim 5, wherein the stimulation light beams and the auxiliary stimulation light beams respectively have frequencies that are different from each other.

8. The optical therapeutic apparatus according to claim 1, wherein said array of light emitters consists of LEDs (Light Emitting Diodes) or laser modules.

9. The optical therapeutic apparatus of claim 1, wherein each of the array of light emitters emits light at constant energy.

10. The optical therapeutic apparatus according to claim 1, wherein each of the pair of ear shields is provided with a circular soft cushion at an exterior portion thereof for tightly abutting against the wearer's ear.

11. The optical therapeutic apparatus according to claim 1, wherein ones of the array of light emitters emit light at varying energy.

12. The optical therapeutic apparatus according to claim 1, wherein ones of the array of light emitters emit light at a constant frequency.

13. The optical therapeutic apparatus according to claim 1, wherein the hanging member is provided with a transmission cable for capturing a frequency signal from a sound producing device and transferring the frequency signal to each of the pair of loud speakers for broadcasting the therapeutic sound or music.

14. The optical therapeutic apparatus according to claim 13, wherein the transmission cable is coupled electrically to a power source in order to obtain an electrical power for illuminating the array of light emitters.

15. The optical therapeutic apparatus according to claim 1, wherein the hanging member is in the form of an adjustable curve structure.

16. The optical therapeutic apparatus according to claim 1, wherein the hanging member is provided with an activation switch coupled electrically to the array of light emitters for switching-on and switching-off of the array of light emitters.

17. The optical therapeutic apparatus according to claim 1, wherein the hanging member further includes a buzzer for generating a reminding alarm at a pre-set time interval.

18. An optical therapeutic apparatus, comprising:

an array of light emitters adapted to each of a wearer's ears in juxtaposed opposition to a plurality of auricular acupuncture points respectively, wherein the array of light emitters includes a plurality of acupoint-stimulation elements corresponding to an auricular acupuncture point of Shenmen and at least one of the other auricular acupuncture point, at least two acupoint-stimulation elements emitting a respective stimulation light beams at different respective time intervals, wherein at least one time interval overlaps with another, and wherein wave lengths of the stimulation light beams ranges from about 450 nm to about 1000 nm;

an ear shield for covering each of the wearer's ears, and wherein each of the ear shields is provided a loud speaker for broadcasting one of sound or music; and a hanging member including a connection portion connects both ear shields, the hanging member further including a display screen for displaying a radiating time and a function selection interface, a regulator knob operable to alter the radiating time and to operate the function selection interface, and a control module coupled to the array of light emitters, both loud speakers, the display screen, and the regulator knob; and a detection unit electrically coupled to the control module, the detection unit transmitting a signal to the control module to activate the array of light emitters when presence of the wearer's ear is detected and deactivate the array of light emitters when absence of the wearer's ear is detected.

19. The optical therapeutic apparatus according to claim 18, wherein the plurality of stimulation light beams emitted from the at least two auricular acupoint-stimulation elements respectively have frequencies that are different from another, and the plurality of stimulation light beams are emitted with varying intensity.

\* \* \* \* \*

UNITED STATES PATENT AND TRADEMARK OFFICE
CERTIFICATE OF CORRECTION

| | | |
|---|---|---|
| PATENT NO. | : 9,517,356 B2 | Page 1 of 1 |
| APPLICATION NO. | : 13/622800 | |
| DATED | : December 13, 2016 | |
| INVENTOR(S) | : Craig Nabat and Chung-Yang Mike Chen | |

It is certified that error appears in the above-identified patent and that said Letters Patent is hereby corrected as shown below:

On the Title Page

Insert -- (30) Foreign Application Priority Data
Jun. 29, 2012 (TW)................................101212599 A --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*